United States Patent [19]
Lin et al.

[11] Patent Number: 5,792,422
[45] Date of Patent: Aug. 11, 1998

[54] LIQUID/VAPOR STERILIZATION CONTAINER SYSTEMS

[75] Inventors: Szu Min Lin, Laguna Hills; Paul Taylor Jacobs, Trabuco Canyon; Su-Syin Wu, Irvine, all of Calif.

[73] Assignee: Ethicon, Inc., Somerville, N.J.

[21] Appl. No.: 771,046

[22] Filed: Dec. 20, 1996

[51] Int. Cl.[6] .............. A61L 2/00; B08B 3/04; B65D 1/34; B65D 1/36

[52] U.S. Cl. .............. 422/31; 422/300; 422/29; 422/294; 422/305; 134/186; 206/363; 206/364; 206/438; 206/439; 206/562; 206/563; 206/564

[58] Field of Search .............. 134/105, 186, 134/901; 422/27, 31, 300, 33, 29, 22, 294, 305; 206/363, 364, 438, 439, 562, 563, 564; 210/210

[56] References Cited

U.S. PATENT DOCUMENTS

| | | | |
|---|---|---|---|
| 1,187,498 | 6/1916 | Castle | 422/300 |
| 2,018,651 | 10/1935 | Bates | 206/370 |
| 2,214,946 | 9/1940 | Werner | 422/293 |
| 2,733,684 | 2/1956 | Trenchard | 119/526 |
| 3,334,768 | 8/1967 | Martin | 220/517 |
| 4,046,254 | 9/1977 | Kramer | 206/370 |
| 4,207,286 | 6/1980 | Boucher | 422/21 |
| 4,732,187 | 3/1988 | Monch | 134/135 |
| 4,900,519 | 2/1990 | Nichols | 422/292 |
| 4,941,585 | 7/1990 | Hare et al. | 220/23.2 |
| 4,959,199 | 9/1990 | Brewer | 422/300 |
| 5,007,232 | 4/1991 | Caudill | 53/526 |
| 5,091,343 | 2/1992 | Schneider et al. | 422/297 |
| 5,174,970 | 12/1992 | Santasalo | 422/292 |
| 5,217,698 | 6/1993 | Siegel et al. | 422/295 |
| 5,307,695 | 5/1994 | Sawchuk | 73/864.51 |
| 5,441,707 | 8/1995 | Lewis et al. | 422/300 |
| 5,518,892 | 5/1996 | Naquil et al. | 435/29 |
| 5,590,777 | 1/1997 | Weiss et al. | 206/439 |

*Primary Examiner*—Robert J. Warden
*Assistant Examiner*—Alex Noguerda
*Attorney, Agent, or Firm*—Andrew C. Farmer

[57] ABSTRACT

A tray and process for hydrogen peroxide vapor sterilization of medical articles. The tray includes a bottom surface and side walls defining a space to receive articles to be sterilized. The bottom surface of the tray includes a number of inlet passages and wells with a known volume. In the process of the present invention, articles to be sterilized are placed in the tray, and aqueous solutions of hydrogen peroxide is delivered into the tray. When the excess hydrogen peroxide is drained through the inlet passages, a known volume of peroxide remains in the wells. Such remaining hydrogen peroxide is then vaporized to achieve sterilization.

37 Claims, 9 Drawing Sheets

LIQUID/VAPOR STERILIZATION CONTAINER SYSTEMS

BACKGROUND OF THE INVENTION

1. Field of the Invention

This invention relates to an apparatus and process for using hydrogen peroxide vapor to sterilize articles such as medical instruments, and more particularly, to the use of liquid hydrogen peroxide and a container system for such a process.

2. Description of the Related Art

Modern medical and dental practices require the use of aseptic materials and devices, i.e., the materials and devices must be generally free from germs, bacteria, etc., and many of these devices are meant for repeated use. In order to achieve this asepsis, efficient sterilization processes are needed for treatment of reusable materials and devices. These processes are needed not only at hospitals and dental offices, but also at the manufacturers of these materials and devices.

Medical instruments have traditionally been sterilized using either heat, as is provided by steam, or a chemical, such as formaldehyde or ethylene-oxide gas or vapor state. Each of these methods has drawbacks. Many medical devices, such as fiber optic devices, endoscopes, power tools, etc., are sensitive to heat, moisture, or both. Formaldehyde and ethylene oxide are both toxic gases that pose a potential hazard to health care workers. Problems with ethylene oxide are particularly severe, because its use requires long aeration times to remove the gas from articles that have been sterilized. This makes the sterilization cycle time undesirably long.

Sterilization using hydrogen peroxide has been shown to have some advantages over other chemical sterilization processes. In the prior art, many sterilization methods use hydrogen peroxide either in the form of liquid solutions or in the form of hydrogen peroxide vapor that has been generated from a liquid solution of hydrogen peroxide.

The sterilization of articles in liquid solutions of hydrogen peroxide can be achieved using a wide variety of methods. In one application, articles to be sterilized can be simply dipped into the liquid hydrogen peroxide solutions. In another application, articles can be first placed onto a perforated tray and then immersed into the liquid hydrogen peroxide solution to achieve sterilization. An example of this type of perforated tray is shown in patent to Casle, U.S. Pat. No. 1,187,498. A more complicated prior art application is, however, disclosed in patent to Schneider et al., U.S. Pat. No. 5,091,343. This patent describes a liquid sterilization apparatus using a removable container to receive articles to be sterilized. The container includes apertures to receive and drain liquid sterilants. During the process, the container is placed into a housing inside the sterilization apparatus. A liquid sterilant solution is pumped into this housing filling the housing and the container thereby treating articles inside the container. At the end of the sterilization cycle, the liquid sterilization cycle, the liquid sterilant is completely drained and the container is removed.

In the prior art, aqueous solutions of hydrogen peroxide are used to generate sterilizing hydrogen peroxide vapor in vacuum chambers to sterilize articles. During the sterilization process, articles to be sterilized are exposed to the hydrogen peroxide vapor. Accordingly, one major parameter of the process needed to achieve satisfactory sterilization is the amount of liquid hydrogen peroxide entering into the chamber to be evaporated. In fact, the amount of liquid peroxide utilized in the system directly affects the sterilization process. For the efficiency of the sterilization process, it is important that the liquid peroxide be delivered to the chamber in measured quantities or volumes.

SUMMARY OF THE INVENTION

One aspect of the present invention relates to a system for sterilization of articles using liquid sterilant. This system includes a bottom surface to receive the articles to be sterilized and at least one well formed in the bottom surface which defines a known volume. The well is positioned so that when the liquid is introduced onto the bottom surface, a known volume of the liquid sterilant fills the well and when the liquid sterilant is drained from the surface, the known volume of liquid sterilant remains in the well so that a subsequent sterilization process can be performed on the articles positioned on the bottom surface with the known volume of liquid sterilant positioned within the bottom surface. The system also includes a heat source or a vacuum source for vaporizing the liquid sterilant in the well, and can optionally include a source of plasma. The bottom surface preferably has at least one perforation for draining the liquid sterilant from the bottom surface. The system also can include a plurality of sidewalls attached to the bottom surface, so that the bottom surface and the plurality of sidewalls define a space. The well formed in the bottom surface can be curved, flat or angled. Thus, the well can be an inwardly extending hemispherical projection. The well can also be formed in the bottom surface as an inwardly extending rectangular projection having rounded ends. In another embodiment, the system includes at least one upwardly extending projection adjacent the well. The well formed in the bottom surface can also be a rectangular box having side walls, defining an opening. Where perforations are provided, they can be disposed adjacent the well, and can be roughly spherical in shape. The upwardly extending projection can include a perforation thereon, which can be on top of the projection or on a side of the projection. The bottom surface can be a sloped surface, a convex or concave surface or a V-shaped surface. The bottom surface is comprised can be of a variety of materials including stainless steels, aluminum, aluminum alloys, liquid crystal polymers, polyesters, polyolefin polymers or fluorinated polyolefins. If the bottom surface is comprised of a composite material, the composite material can include a filler of high thermal conductivity. Examples of composite materials include a metal-filled polymer, a ceramic-filled polymer and a glass-filled polymer. The liquid sterilant is preferably liquid hydrogen peroxide.

Another aspect of the present invention relates to method for sterilization of an article. This method includes placing the article on a bottom surface having one or more wells formed therein. Each of the wells defines a known volume. The method also includes introducing liquid sterilant onto the bottom surface, thereby filling the one or more wells with the known volume of sterilant, and vaporizing the known volume of sterilant in the one or more wells, thereby sterilizing the article using the vaporized liquid sterilant. The introducing step can include immersing the bottom surface into the liquid sterilant, thereby filling the one or more wells, removing the bottom surface from the liquid sterilant, and draining the liquid sterilant from the bottom surface, whereby the known volume of liquid sterilant remains in the one or more wells. The bottom surface can include one or more perforations extending therethrough, and a plurality of sidewalls in contact with the bottom surface such that the bottom surface and the plurality of sidewalls define a space. Thus, the introducing step can include flowing the liquid sterilant through the perforations onto the bottom surface to thereby contact with the article, and draining the sterilant through the inlet passages. The article can have a lumen therein, and the introducing step can include attaching an adaptor to the lumen and flowing the liquid sterilant through the adaptor and into the lumen. The liquid sterilant preferably comprises hydrogen peroxide. The sterilization can include placing the bottom surface with the article and known volume of sterilant in a diffusion-restricted environment. Thus, the sterilizing can include exposing the diffusion-restricted environment to vacuum for a period of time. The known quantity of the liquid sterilant ordinarily vaporizes during the sterilizing, and the sterilizing ordinarily occurs within a chamber. A suitable diffusion restricted environment can be provided as a diffusion restricted container. The method can include enclosing the article within a gas permeable material, which can be performed before the vaporizing step. The article can also be enclosed within a gas permeable pouch or container. Thus, both the article and the bottom surface can be enclosed within the gas permeable material, such as CSR-wrap or TYVEK™. The vaporizing step can include heating or reducing pressure. The method can also include exposing the article to plasma after the vaporizing step to enhance efficacy of sterilization and/or remove residual sterilant.

BRIEF DESCRIPTION OF THE DRAWINGS

FIGS. 6A(1)–6C(4) cross sectional views of wells and the upward projections;

DETAILED DESCRIPTION OF THE PREFERRED EMBODIMENT

Sterilizing lumened devices or other articles has always posed a challenge to sterilization systems. The system of the present invention is directed to the use of both liquid and vapor phase sterilants to sterilize articles. In the present invention, a hydrogen peroxide solution is used to perform the sterilization process of the present invention. During the sterilization process, articles are first pretreated with the liquid hydrogen peroxide and then exposed to a vacuum to vaporize a predetermined volume of liquid hydrogen peroxide. One such example of a sterilization system that pretreats articles with liquid peroxide before vapor phase sterilization is disclosed in copending application to the applicant, U.S. Ser. No. 08/628,965, entitled "Method of Sterilization Using Pretreatment with Hydrogen Peroxide". The entire contents of this copending application are hereby incorporated by reference. However, this system is described only in connection with diffusion-restricted environments. As used herein, a "diffusion-restricted" area refers to any one or more of the following properties: (1) the ability of the area of an article placed within the sterilization system of the present invention to retain 0.17 mg/L or more hydrogen peroxide solution after one hour at 40° C. and 10 torr; (2) having the same or more diffusion restriction than provided by a single entry/exit port of 9 mm or less in internal diameter and 1 cm or greater in length; (3) having the same or more diffusion restriction than provided by a lumen 27 cm in length and having an internal diameter of 3 mm; (4) having the same or more diffusion restriction than provided by a lumen having a ratio of length to internal diameter greater than 50; (5) the ability of an article placed within the sterilization system of the present invention to retain 17% or more of the hydrogen peroxide solution placed therein after one hour at 40° C. and 10 torr; or (6) being sufficiently diffusion-restricted to completely sterilize a stainless steel blade within a 2.2 cm by 60 cm glass tube having a rubber stopper with a 1 mm by 50 cm stainless steel exit tube therein at a vacuum of 10 torr for one hour at 40° C. in accordance with the present invention. It is acknowledged that characteristics (1) and (5) will vary depending on the initial concentration of hydrogen peroxide placed into the article; however, this can be readily determined by one having ordinary skill in the art.

The system described by the inventors in their previous application is not able to provide a predetermined liquid peroxide to vaporize. In the process of the present invention, articles to be sterilized are first placed in a sterilization container. Next, the hydrogen peroxide solution is delivered into contact with articles in the container so that articles can be treated with the liquid peroxide. As a first sterilization step in the process, this treatment in liquid peroxide is called pretreatment. In this respect, the delivery of the liquid peroxide into contact with articles may be facilitated through means such as flowing the peroxide into the container, submerging the container into the peroxide or spraying the peroxide onto articles in the container. As will be described more fully hereinbelow, the sterilization container is configured to retain a certain volume of liquid hydrogen peroxide in the container when the rest of the liquid hydrogen peroxide is drained. Such retained hydrogen peroxide is then vaporized in an evacuated chamber to achieve sterilization. Several embodiments of the sterilization container are set forth below.

Figure 1A:
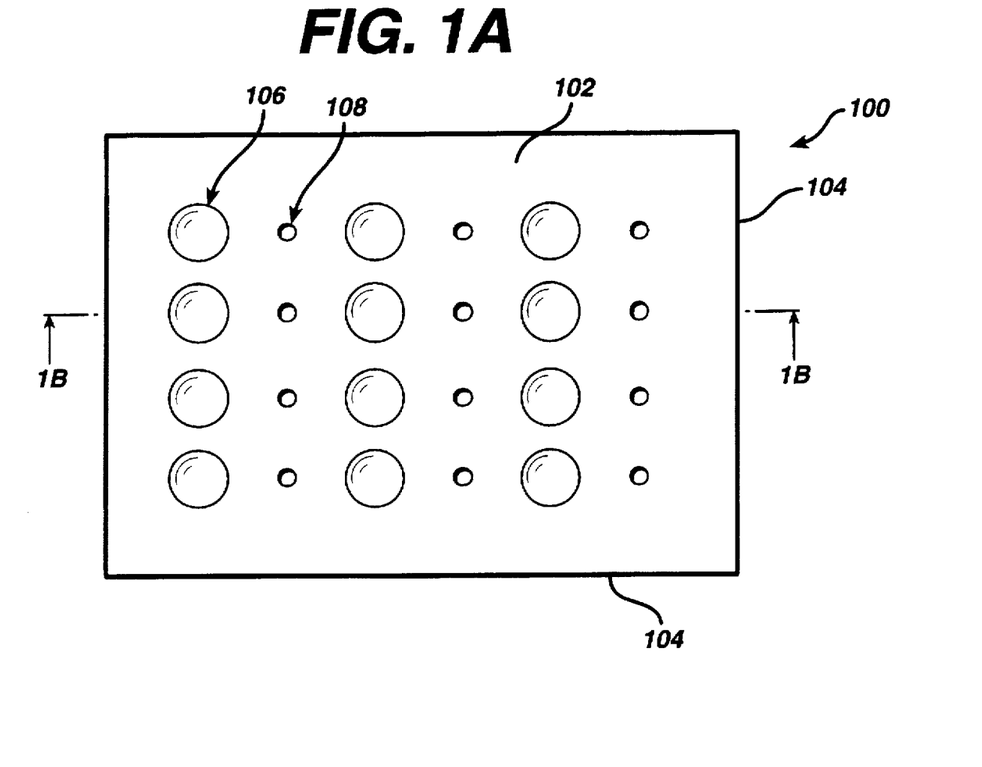
FIG. 1A is a schematic top view of a first embodiment of a liquid peroxide tray.
Figure 1B:
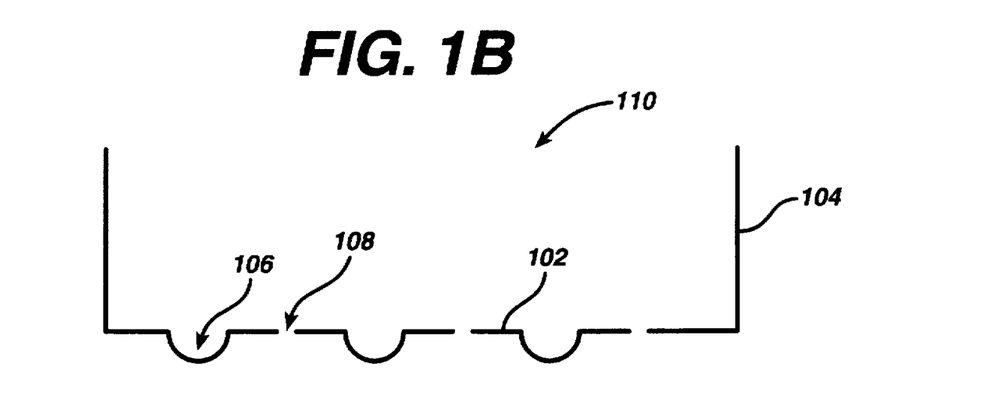
FIG. 1B is a cross-sectional view of the liquid peroxide tray shown in FIG. 1A.

Reference will now be made to the drawings wherein like numerals refer to like parts throughout. As illustrated in FIG. 1A, in the preferred embodiment the sterilization container of the present invention may be configured as a tray 100. The tray 100 comprises a base plate 102 and a peripheral side-wall 104 which is preferably perpendicularly attached to the periphery of the base plate 102. The base plate 102 and the side wall 104 define a cavity 110 of the tray 100 to receive the articles to be sterilized. As shown in FIGS. 1A and 1B, the base plate 102 of the tray 100 preferably comprises a plurality of evenly spaced wells 106 and perforations 108. In this embodiment, wells 106 are preferably configured to have a hemispherical shape; however, as discussed in more detail hereinbelow in conjunction with FIGS. 6A(1)-6C(4), the shape of the wells 106 can take any of a variety of forms. The wells 106 are downwardly projected to the plane of the base plate 102 in a manner shown in FIG. 1B. These wells 106 are dimensioned to hold a desired volume of liquid hydrogen peroxide. Perforations 108 are disposed evenly adjacent to wells 106 on the tray 100. It will be apparent from the foregoing that perforations 108 render the tray 100 permeable to fluids and therefore permit washing of the articles in the tray 100 with liquids. In the preferred embodiment these perforations 108 enable the tray 100 to drain the liquid peroxide which has been delivered into contact with the articles in the tray 100.

The perforations also enable the tray to be immersed into the liquid hydrogen peroxide so that the articles in the tray 100 can be washed with the liquid peroxide. However, when the excess liquid peroxide is drained through the perforations 108, a predetermined volume of the liquid peroxide remains in the wells 106. Since the wells 106 of the tray 100 have a predetermined volume, the amount of the remaining hydrogen peroxide in these wells 106 is known. However, as is well known in the art, volume of a liquid in a container also depends on the surface tension of the liquid and the material of the container. Additionally, temperature will affect the surface tension and density of the liquid, which would also affect the volume. As will be explained in detail hereinbelow, this remaining liquid peroxide will be vaporized during the following sterilization process.

Figure 2A:
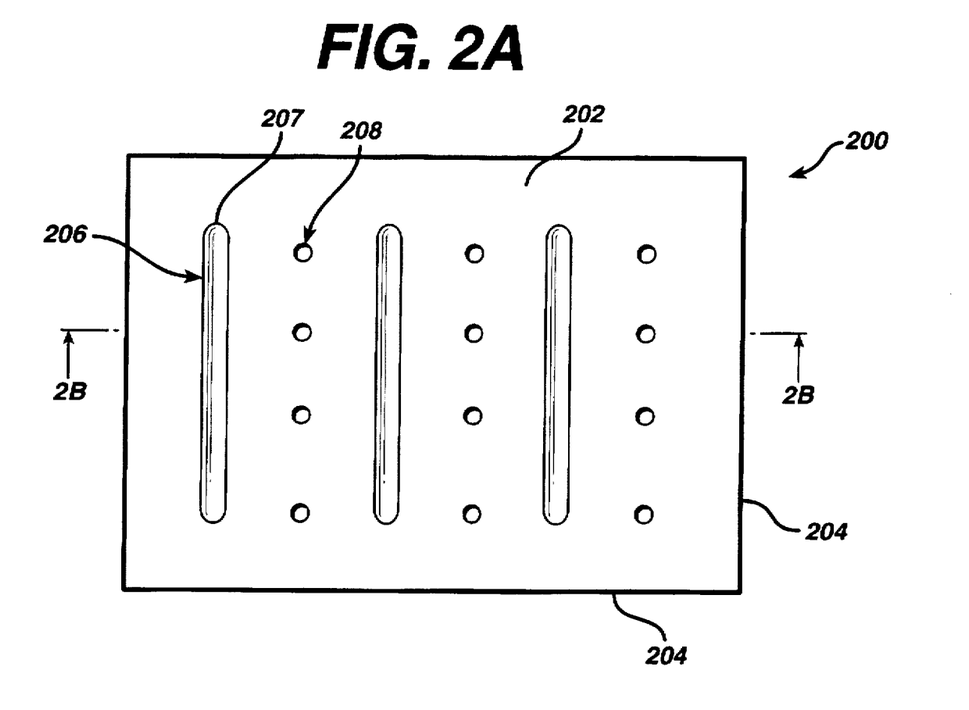
FIG. 2A is a schematic top view of a second embodiment of the liquid peroxide tray.
Figure 2B:
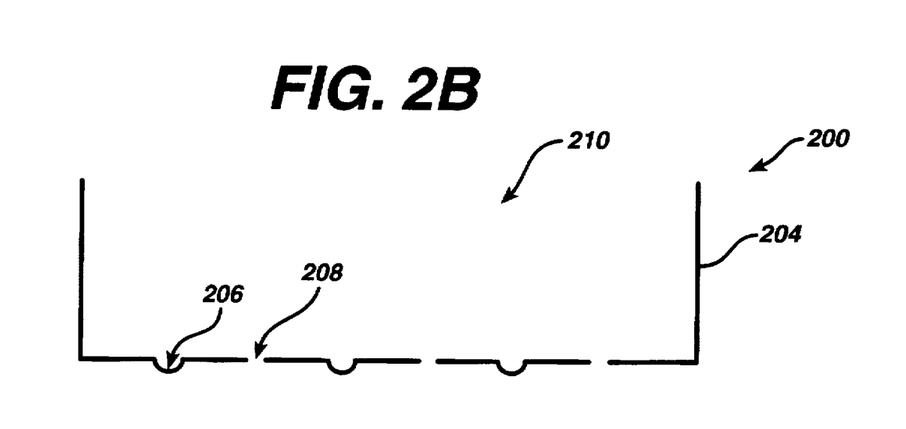
FIG. 2B is a cross-sectional view of the liquid peroxide tray shown in FIG. 2A.

FIG. 2A shows a second embodiment of the peroxide tray with the tray 200 comprising a base plate 202 and a peripheral side-wall 204. Similar to the first embodiment, the peripheral side-wall 204 is attached to the periphery of the base plate 202. Preferably, the side-wall 204 is attached perpendicular to the base plate 202. As shown in FIGS. 2A and 2B, the base plate 202 and the side-wall 204 define a cavity 210 to receive articles to be sterilized. The base plate 202 of the tray 200 can comprise a plurality of evenly spaced wells 206 and perforations 208. In this embodiment, the wells 206 are configured to have a rectangular shape with rounded ends 207, and are downwardly projected to the plane of the base plate 202 of the tray 200. The wells 206 are preferably positioned transversely relative to the longitudinal axis of the tray 200 in a manner shown in FIGS. 2A-2B. As is explained in the first embodiment, these wells 206 are dimensioned to retain a predetermined amount of liquid peroxide when the peroxide is drained. Perforations 208 are disposed evenly adjacent to the wells 206 in a manner shown in FIGS. 2A-2B. As is explained in detail in the first embodiment, perforations 208 allow the liquid peroxide to fill the tray 200 and then drain the liquid peroxide from the tray 200.

Figure 3A:
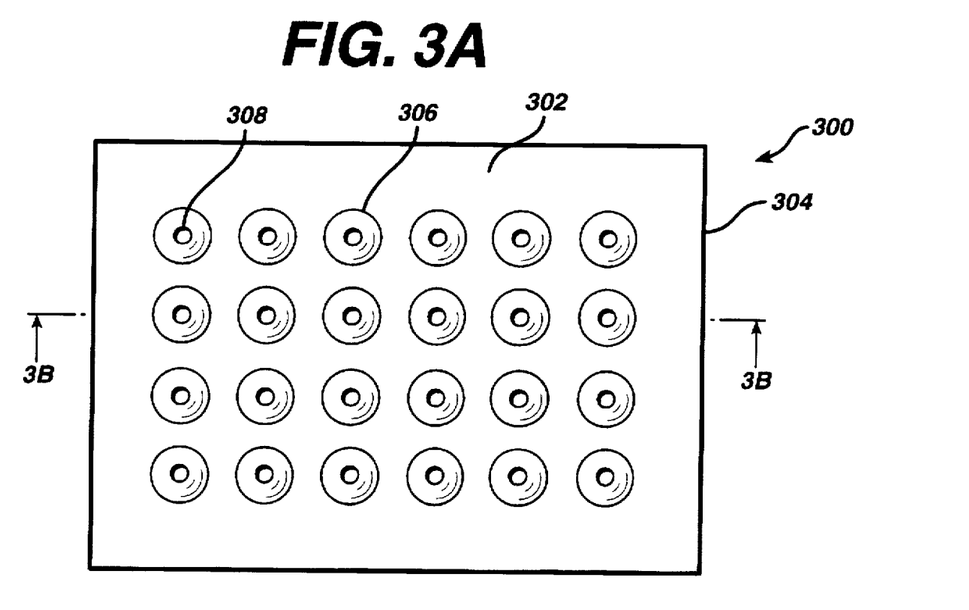
FIG. 3A is a schematic top view of a third embodiment of the liquid peroxide tray.
Figure 3B:
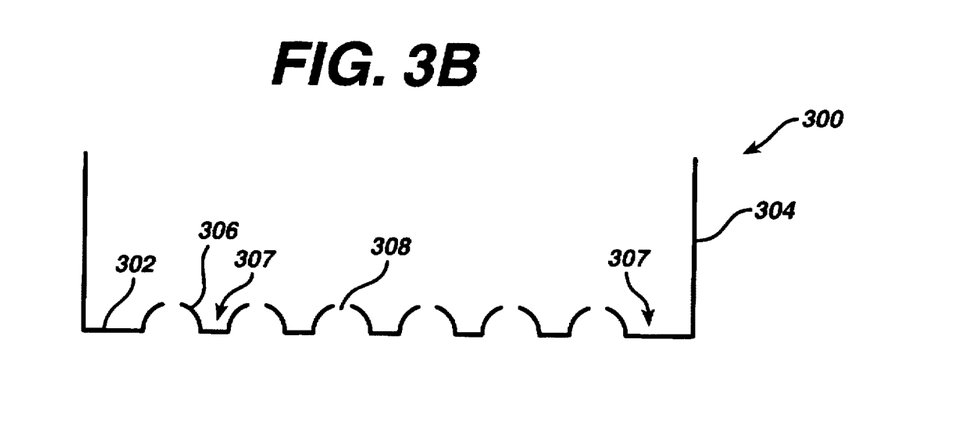
FIG. 3B is a cross-sectional view of the liquid peroxide tray shown in FIG. 3A.

As shown in FIG. 3A, in a third embodiment, a tray 300 comprising a base plate 302 and a peripheral side wall 304 is configured as is explained in the previous embodiments. As shown in FIGS. 3A-3B, the base plate 302 of the tray 300 comprises a plurality of upwardly extending projections 306. In this embodiment, these projections 306 are preferably configured to have a hemispherical shape and are upwardly extended on the plane of the base plate 302 as in the manner shown in FIGS. 3A-3B. As shown in FIGS. 3A-3B, the tops of the projections are perforated to render the tray 300 permeable to fluids. In this embodiment, although perforations 308 facilitate the draining of the liquid peroxide from the tray 300, the remaining liquid peroxide is retained in a space 307 defined by the outer surface of the projections 306 and peripheral side-wall 304 of the tray as well as the upper surface of the base plate 302. Since the volume occupied by projections and the depth of the liquid peroxide (level of perforations) are known, the amount of peroxide retained in the tray 300 can easily be determined.

Figure 4A:
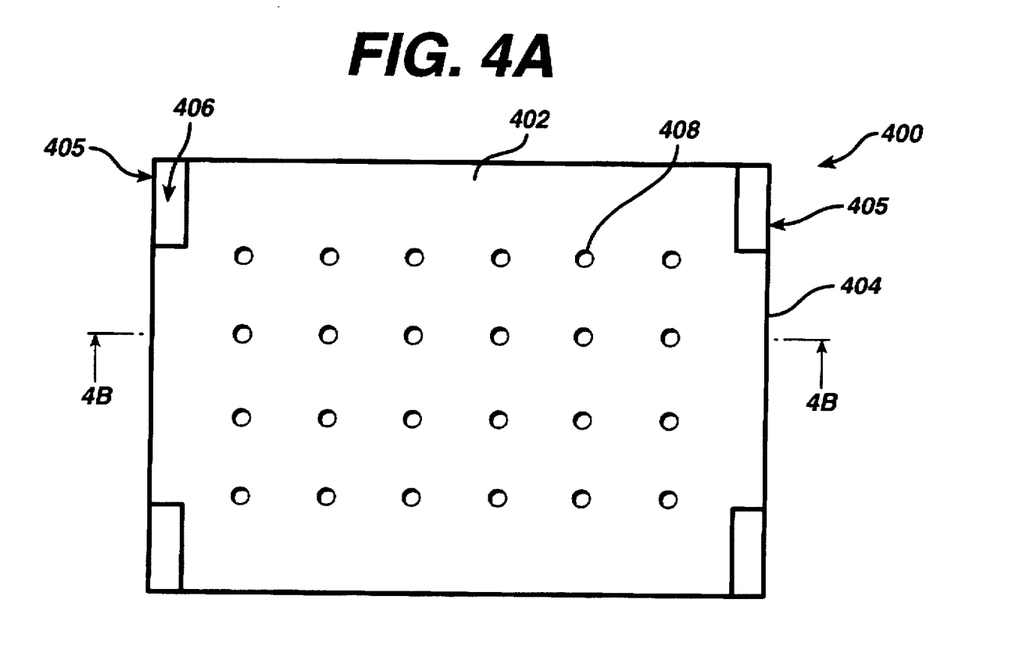
FIG. 4A is a schematic top view of a fourth embodiment of the liquid peroxide tray.
Figure 4B:
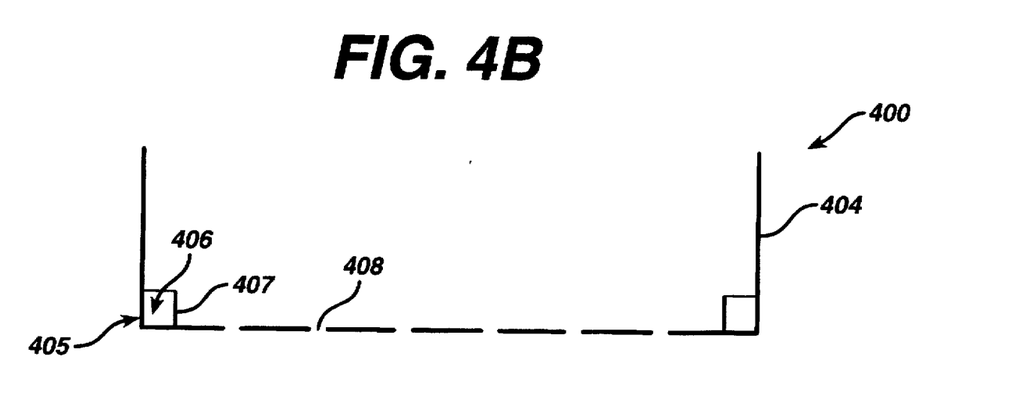
FIG. 4B is a cross-sectional view of the liquid peroxide tray shown in FIG. 4A.

As shown in FIG. 4A, in a fourth embodiment, a tray 400 comprising a base plate 402 and a peripheral side wall 404 is constructed in a manner described in the previous embodiments. As shown in FIGS. 4A-4B, the base plate 402 of the tray 400 may comprise a plurality of wells 406 and perforations 408. In this embodiment, the wells 406 are preferably constructed as open containers comprising a wall section 407 which is perpendicular to the surface of the base plate 402. As shown in FIG. 4A, both ends of the wall section 407 may terminate on the peripheral side wall 404 so that the well 406 is surrounded by both a portion 405 of the peripheral wall 404 and the wall section 407. In this embodiment, wells are located at the inner corners of the tray 400 and have a rectangular shape. Perforations 408 are disposed evenly over the base plate 402 as in the manner shown in FIGS. 4A-4B.

Figure 5A:
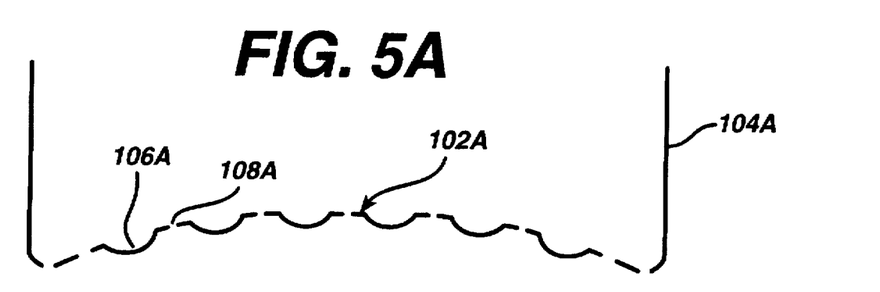
FIG. 5A is a cross-sectional view of an alternative embodiment of the liquid peroxide tray wherein the bottom surface of the liquid peroxide tray has been configured to have a convex shape.
Figure 5B:
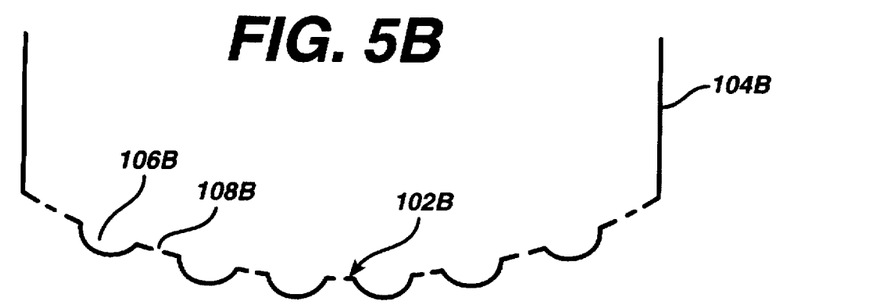
FIG. 5B is a cross-sectional view of an alternative embodiment of the liquid peroxide tray wherein the bottom surface of the liquid peroxide tray has been configured to have a concave shape.
Figure 5C:
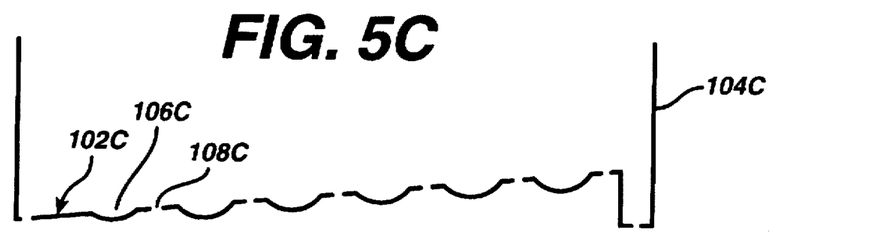
FIG. 5C is a cross-sectional view of an alternative embodiment of the liquid peroxide tray wherein the bottom surface of the liquid peroxide tray has been configured to have a slope.
Figure 5D:
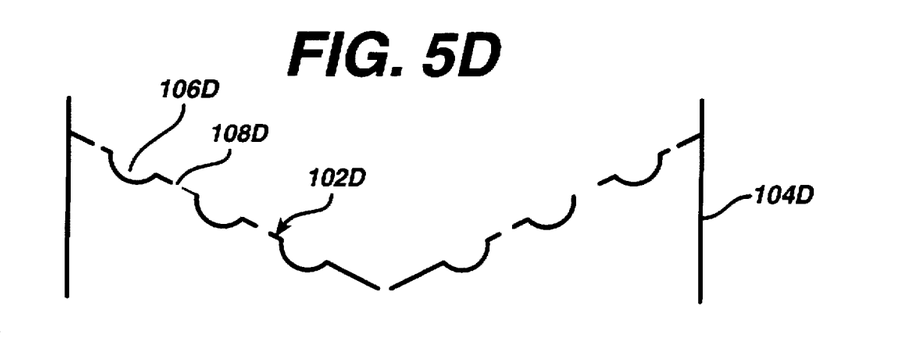
FIG. 5D is a cross sectional view of an alternative embodiment of the liquid peroxide tray wherein the bottom surface of the liquid peroxide tray is has been configured to have V-shape.
Figure 5E:
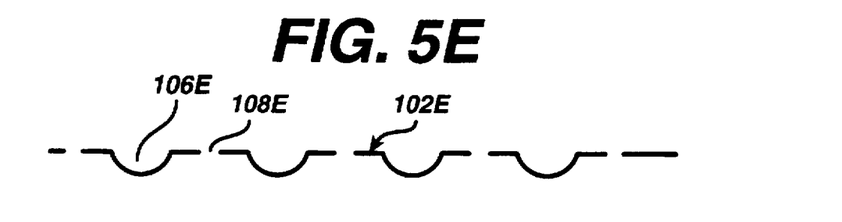
FIG. 5E is a cross sectional view of an alternative embodiment of the liquid peroxide tray without peripheral side-wall.

Although these are several embodiments to construct the liquid peroxide trays, it is understood by those skilled in the art, that the peroxide trays can also be advantageously manufactured in numerous alternative ways. As illustrated in cross-section in FIG. 5A, for the preferred embodiment, a base plate 102A of a peroxide tray 100A can be configured to have a convex shape so that faster draining through perforations 108A can be provided. Similarly, FIG. 5B illustrates the plate 102B of a peroxide tray 100B which has a concave shape. As shown in FIG. 5C, a base plate 102C of a peroxide tray 100C can be configured to have a slope to provide faster draining. Further, as shown in FIG. 5D, the base plate 102D of a peroxide tray 100D can be configured to have a V-shape in the manner shown in FIG. 5D. The base plate 102D can also be configured to have a reverse V-shape (not shown). Such convex, concave, inclined, V-shape and reverse V-shape base plate designs may enhance draining of liquid peroxide from the tray, and hence from the surface and the inner lumen of the instruments. Alternatively, as illustrated in FIG. 5E, a tray 100E may be comprised of a base plate 102E without a peripheral side-wall. However, the tray 100E may include a pair of handle means (not shown) attached to the sides of the tray 100E. A handle mean can, for example, be a wire frame. The base plate 102E of the tray 100E comprises wells 106E and perforations 108E. In this alternative embodiment, fluid is retained within the wells 106E and drained off the sides of the base plate 102E; however, the base plate 102E can also include perforations 108E to facilitate draining. The base plate 102E can also take a non-planar shape to facilitate drainage of fluid.

Figure 6A:
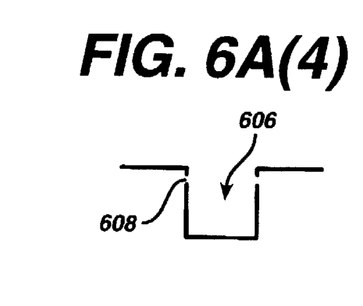
Figure 6B:
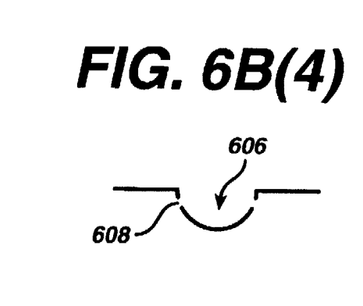
Figure 6C:
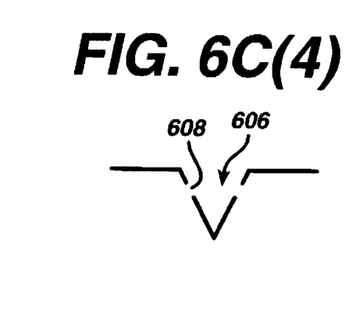

In accordance with the principles of the present invention, wells and the upward projections as well as accompanying perforations can be configured in a wide variety of shapes. Examples of these shapes are illustrated in FIGS. 6A(1)–6C(4). As illustrated in FIGS. 6A(1)–6C(1) the upwardly extending projections may comprise various profiles. The perforations 608 are disposed on top of the projections 607 as in the manner shown in FIGS. 6A(1),6B(1) and 6C(1). As illustrated in FIGS. 6A(2), 6B(2) and 6C(2), perforations may be distributed 608 evenly around wells 606 as in the manner shown in FIGS. 6A(2), 6B(2) and 6C(2). In FIGS. 6A(3), 6B(3), 6C(3), 6A(4), 6B(4) and 6C(4), perforations 608 are alternatively disposed around the top ends of both wells 606 and the upward projections 607 as in the manner shown in FIGS. 6A(3), 6B(3), 6C(3), 6A(4), 6B(4) and 6C(4).

In the preferred embodiment, the tray 100 can be manufactured from any material which has minimum interaction with hydrogen peroxide. In this respect, the tray material should have a minimal hydrogen peroxide absorption or decomposition. Examples of common materials used to manufacture the tray 100 include, but are not limited to, metallic materials and polymeric materials. Metallic materials may preferably be stainless steels such as 304, 316, 304L and 316L (in AISI standards), and aluminum and aluminum alloys. Preferred polymeric materials may be reinforced or unreinforced materials such as liquid crystal polymers reinforced with a filler of high thermal conductivity, polyolefin polymers and fluorinated polyolefins. A liquid crystal polymer may be a polyester including wholly aromatic polyester such as VECTRA™ (Hoechst-Celenese) or a poly ethylene teraphthalate (PET) such as THERMX™ (Eastern Chemical). Polyolefin polymers may include high or low density polyethylene, polypropylene and polybutylene. An exemplary fluorinated polyolefin polymer may be TEFLON™. In the preferred embodiment, a tray material may comprise either a material with a high thermal conductivity to enhance heat transfer or a material reinforced with high thermal conductivity metal, ceramic or glass. Among the above mentioned materials, stainless steels, aluminum and aluminum alloys, as well as liquid crystal polymers reinforced with a filler of high thermal conductivity, are preferred high thermal conductivity materials. The tray can be made using techniques well known in the art.

As previously mentioned, the process of the present invention involves both liquid and vapor phase sterilization process steps. In either process, however, articles to be sterilized are contained and transported in the peroxide tray 100 of this invention. In the method of the present invention, articles in the tray 100 (FIG. 1A) may be first treated with liquid sterilant, such as hydrogen peroxide, by delivering dilute, aqueous solutions of hydrogen peroxide into the tray 100. In one embodiment, the liquid peroxide is delivered by immersion of the tray 100A into the liquid sterilant. In this step of treatment with liquid sterilant, the articles in the tray 100 contact with the liquid sterilant so that the inner and outer surfaces of the articles are substantially washed and soaked by the liquid peroxide. In particular, at this step, hydrogen peroxide solution effectively contacts with the inaccessible or hard-to-reach places of the articles. Such articles may include long narrow lumens, hinges and other articles having spaces where diffusion of vapors is restricted.

The aqueous solutions of hydrogen peroxide can be relatively dilute, e.g., as low as 1–6% or lower by weight. In the preferred embodiment, a preferred concentration range for the peroxide solution may be 3–15% by weight, or more preferably 6–10% by weight. As previously explained, when the peroxide solution in the tray 100 is drained through perforations 108 in the bottom plate 102 of the tray 100, a predetermined quantity of hydrogen peroxide can be retained in the wells 106 of the peroxide tray 100. In the second step of the process, this retained hydrogen peroxide and the peroxide remaining in inaccessible spaces of the articles are vaporized to achieve sterilization. This sterilization step can be performed by placing the tray into a sterilization environment such as a vacuum chamber, and subsequently applying vacuum and/or heat to vaporize the peroxide. As is well known in the art, sterilization is not easily achieved through contact with dilute liquid peroxide solutions at low temperatures. However, sterilization can be achieved at low temperatures and in short periods of time upon exposure to hydrogen peroxide vapor under vacuum or vacuum combined with a plasma process. As will be explained more fully hereinbelow, the liquid hydrogen peroxide treatment and the vaporization of the peroxide can also be performed within the same vacuum chamber. Consequently, it would be understood that the present process particularly pretreats the articles in the tray 100 with the liquid peroxide and subsequently vaporizes the retained liquid peroxide in a vacuum chamber to achieve sterilization.

Figure 7A:
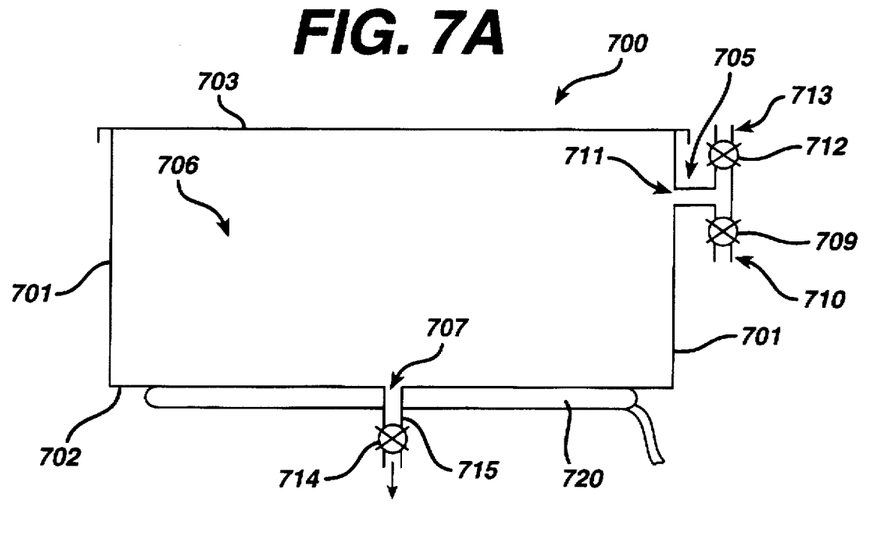
FIG. 7A is a schematic view of a sterilization container the liquid peroxide tray is positioned therein.

The preferred embodiment of the process of the present invention comprises an in-situ sterilization process to achieve the pretreatment and vapor sterilization steps in a sterilization system. As illustrated in FIG. 7A, In-situ sterilization process of the present invention is carried out in a sterilization container 700. The sterilization container 700 comprises a bottom wall 702 and a peripheral side wall 701, and a removable container lid 703 through which articles to be sterilized can be introduced. Preferably, the peripheral side-wall 701 of the container 700 is perpendicularly attached to the periphery of the bottom wall 702. In this embodiment, the bottom wall 702 and the peripheral side-wall 701 define a housing 706 of the container 700. The housing 706 of the sterilization container is preferably configured and dimensioned to receive at least one tray 100 (FIG. 7B) containing articles to be sterilized.

As is shown in FIG. 7A, the peripheral side-wall 701 of the chamber 700 includes a first opening 711 which is preferably connected to a T-connector 705 attached to the side-wall 701. The T-connector connects the container 700 to both a vacuum source and a liquid peroxide source. Therefore, T-connector 705 preferably comprises a first-end 713 to the vacuum source (not shown) and a second-end 710 to the liquid peroxide source (not shown). The first-end 710 of the T-connector 705 contains a first valve 712 or a vacuum valve 712 to isolate the container 700 from the vacuum source. Similarly, the second-end 710 contains a second valve 709 or an inlet valve 710 to isolate the liquid peroxide source from the chamber 700.

As is further shown in the FIG. 7A, the bottom wall of the container 700 comprises a second opening 707 which is connected to an outlet connector 715 which allows the draining of the liquid peroxide from the container 700. The connector 715 include an outlet valve 714 to control the draining of the liquid peroxide. The draining of the liquid peroxide is controlled by opening and closing of the outlet valve 714. The container 700 may also comprise an optional heater 720 which may be attached to bottom wall 702 or/and outside the peripheral wall 701 (not shown) of the container 700, in a manner shown in FIG. 7A.

Figure 7B:
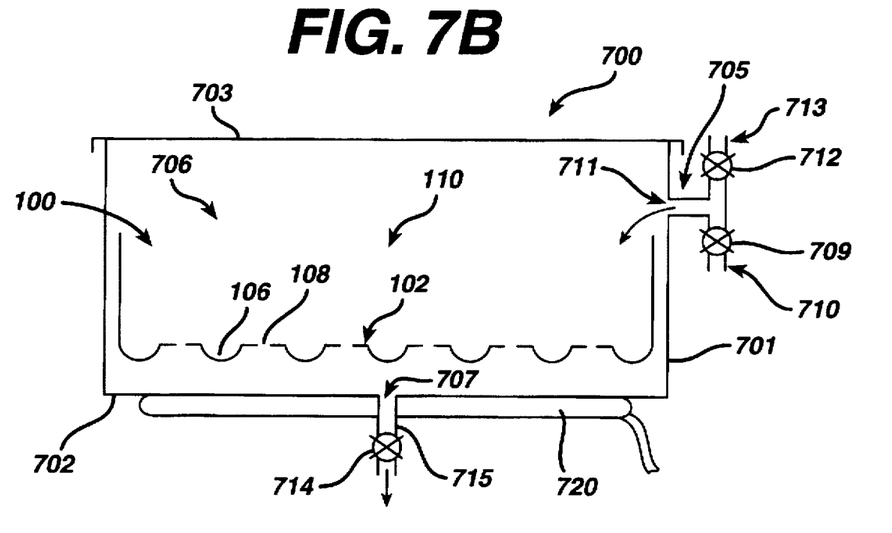
FIG. 7B is a schematic view of the sterilization container in FIG. 7A wherein the liquid peroxide tray shown in FIG. 1A is positioned therein.
Figure 7C:
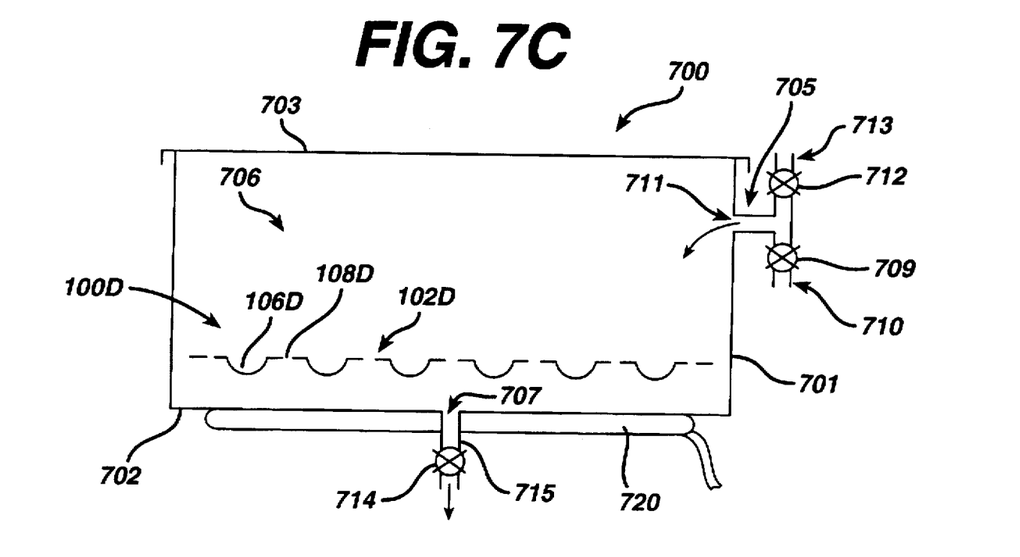
FIG. 7C is a schematic view of the sterilization container in FIG. 7A wherein the liquid peroxide tray shown in FIG. 5E is positioned therein.

The preferred embodiment of the in-situ sterilization process of the present invention is shown in FIG. 7B. As illustrated in FIG. 7B, the tray 100 containing articles to be sterilized is initially placed into the housing 706 of the sterilization container 700. The liquid peroxide is delivered into chamber 700 through opening 711 and fills the container 700, and hence covers articles in the tray 100 to pretreat articles. The articles to be sterilized are then pretreated with liquid peroxide for a required period of time before draining the liquid peroxide through outlet valve 714. The draining of the liquid peroxide is carried out by opening the outlet valve 714. Once the draining is completed, the outlet valve 714 is closed and the container is evacuated to vaporize the liquid peroxide retained in the wells 106 of the tray 100. Articles remain in the peroxide vapor for a period to effect complete sterilization. It will be understood that, for lumened articles, an adaptor can be used to connect flow of liquid peroxide to the interior of the article. As is well known in the art, a wide variety of time, temperature an pressure conditions can be used to effect sterilization. In a second embodiment, in-situ sterilization process can be alternatively carried out using one of the alternative tray embodiments. As illustrated in FIG. 7C, the tray 100D can also be used during the in-situ sterilization process. Absence of peripheral side-walls may facilitate a faster liquid peroxide draining.

Figure 8:
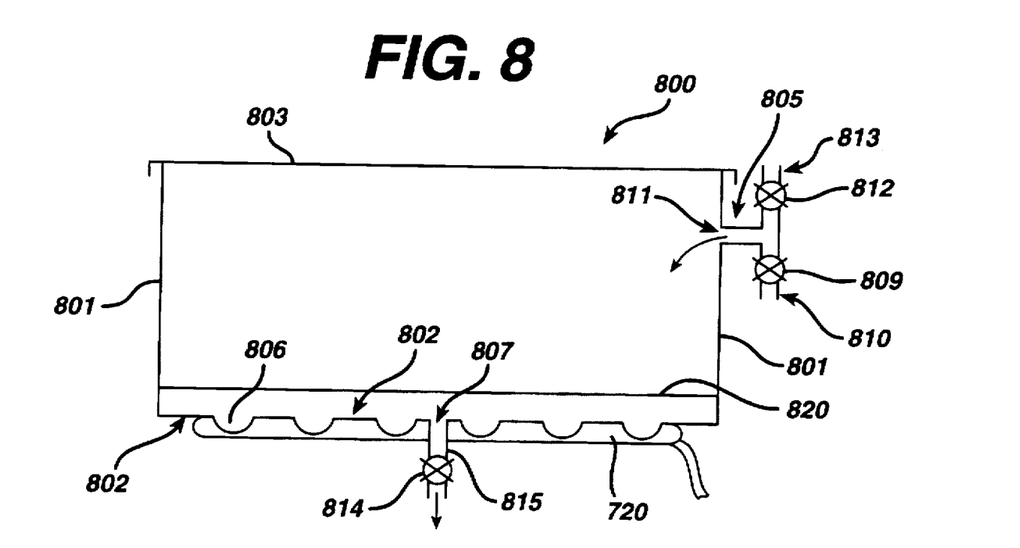
FIG. 8 is a schematic view of an alternative embodiment of the sterilization container.

As shown in FIG. 8, in a third embodiment, in-situ sterilization process can be carried out in an alternative sterilization container 800. Similar to the container 700 of the previous embodiment, the container 800 also comprises a bottom wall, a peripheral side-wall and a container lid as well as other features configured in a manner shown in FIG. 8. However, as a departure from the previous container embodiment, the bottom wall 802 of the container 800 comprise a plurality of wells 806 to retain the liquid peroxide. The liquid peroxide can be drained through opening 807 which is connected to an outlet valve 814 through connector 815. As is understood, the container 800 does not require the use of tray 100 during the sterilization process. Articles to be sterilized can be directly placed into the container 800 and rest of the process flow is proceeded as is explained above. Optionally, a metal grid 820 can be provided to keep the articles to be sterilized out of the liquid sterilant at the bottom of the container 800.

In an alternative process of the present invention, an ex-situ sterilization process can be used to sterilize articles. In this process, the tray 100 containing articles is manually submerged into a liquid hydrogen source such as a liquid hydrogen tank to pretreat articles in liquid peroxide. As previously explained above the tray 100 can carry or retain a predetermined amount of liquid peroxide in the tray 100 when the tray 100 is removed from the liquid peroxide container. Following this step, the tray 100 containing articles and the remaining liquid peroxide is placed into the container 700 or another vacuum chamber. The chamber 700 is sealed and evacuated to vaporize the hydrogen peroxide in the wells 106 of the tray 100. The articles are exposed to hydrogen peroxide vapor for a period of time at a temperature sufficient to effect sterilization.

In an alternative embodiment of the ex-situ sterilization process of the present invention, a similar process is used to treat articles in liquid hydrogen peroxide. As a departure from the previous embodiment, this alternative embodiment may use a CSR-wrap to wrap the tray 100 containing the articles and the remaining hydrogen peroxide. Specifically, the CSR-wrap restricts the diffusion of germs and bacteria, but allows the diffusion of hydrogen peroxide vapor through the CSR-wrap. In the following step, the CSR-wrap wrapped tray 100 is placed into the container 700 and the container is sealed and evacuated to vaporize the hydrogen peroxide to achieve sterilization. In another embodiment, the CSR-wrap can be replaced with a pouch or so that the tray 100 containing articles can be inserted into the this pouch. The pouch can be readily made of a gas permeable material layer. This gas permeable material layer may comprise TYVEK™ materials, including combinations of MYLAR™ and TYVEK™. Alternatively, the tray 100 can be placed into a gas permeable container before placing into the container 700. This gas permeable container may for example be a container having at least one perforation thereon, preferably on a top portion thereof. Alternatively, the container can be fitted with a valve.

Hence, although the foregoing description of the preferred embodiment of the present invention has shown, described and pointed out the fundamental novel features of the invention, it will be understood that various omissions, substitutions, and changes in the form of the detail of the apparatus and method as illustrated as well as the uses thereof, may be made by those skilled in the art, without departing from the spirit of the present invention. Consequently, the scope of the present invention should not be limited to the foregoing discussions, but should be defined by the appended claims.

What is claimed is:

1. An apparatus for sterilization of articles using liquid sterilant, comprising:

a container for holding articles to be sterilized;

a bottom surface in said container;

at least one well formed in said bottom surface which defines a known volume, said well having a lip over which excess liquid in said well will flow to said claim thereby determining said known volume;

a drain on said bottom surface, through which liquid on said bottom surface will drain; and wherein said well is positioned so that when said liquid sterilant is introduced onto said bottom surface, a known volume of said liquid sterilant fills said well and when said liquid sterilant is drained from said surface, said known volume of liquid sterilant remains in said well so that a subsequent sterilization process can be performed on said articles positioned in said container with said known volume of liquid sterilant; and a heat source or a vacuum source for vaporizing the liquid sterilant in said well.

2. The apparatus of claim 1, additionally comprising a source of plasma.

3. The apparatus of claim 1, additionally comprising a plurality of sidewalls attached to said bottom surface, wherein said bottom surface and said plurality of sidewalls define a space.

4. The apparatus of claim 1, wherein said well formed in said bottom surface is curved, flat or angled.

5. The apparatus of claim 4, wherein said well is formed of an upwardly extending hemispherical projection.

6. The apparatus of claim 1, wherein said well is formed of an upwardly extending rectangular projection.

7. The apparatus of claim 1, wherein said well formed in said bottom surface comprises at least one upwardly extending projection adjacent said well.

8. The system of claim 1, wherein said well formed in said bottom surface is a rectangular box having side walls defining an opening.

9. The apparatus of claim 1, wherein said drain comprises one or more perforations through said bottom surface disposed adjacent said well.

10. The apparatus of claim 1, wherein said drain comprises one or more perforations which are roughly round in shape.

11. The apparatus of claim 1, wherein said at least one well is formed of at least one upwardly extending projection and said drain comprises at least one perforation on said at least one upwardly extending projection.

12. The apparatus of claim 11, wherein said perforation is on top of said projection or on a side of said projection.

13. The apparatus of claim 1, wherein said bottom surface is comprised of a sloped surface.

14. The apparatus of claim 1, wherein said bottom surface is comprised of a convex or concave surface.

15. The apparatus of claim 1, wherein said bottom surface is comprised of a V-shaped surface.

16. The apparatus of claim 1, wherein said bottom surface is comprised of a material selected from the group consisting of stainless steels, aluminum, aluminum alloys, liquid crystal polymers, polyesters, polyolefin polymers and fluorinated polyolefins.

17. The apparatus of claim 1, wherein said bottom surface is comprised of a composite material.

18. The apparatus of claim 17, wherein said composite material comprises a filler of high thermal conductivity.

19. The apparatus of claim 17, wherein said composite material is selected from the group consisting of a metal-filled polymer, a ceramic-filled polymer and a glass-filled polymer.

20. The apparatus of claim 1, wherein said liquid sterilant is liquid hydrogen peroxide.

21. A method for sterilization of an article comprising:

placing said article in a container;

providing said container with a bottom surface having one or more wells formed therein, each of said wells defining a known volume;

introducing liquid sterilant onto said bottom surface, thereby filling said one or more wells with said known volume of sterilant;

draining said liquid sterilant through a drain on said bottom surface, whereby said known volume of liquid sterilant remains in said one or more wells; and vaporizing said known volume of sterilant in said one or more wells, thereby sterilizing said article using the vaporized liquid sterilant.

22. The method of claim 21, wherein:

the introducing step comprises immersing said bottom surface into said liquid sterilant, thereby filling said one or more wells; and said draining step comprises removing said bottom surface from said liquid sterilant and draining said liquid sterilant from said bottom surface, leaving said known volume of liquid sterilant in said one or more wells.

23. The method of claim 22, wherein said bottom surface further comprises:

one or more perforations extending therethrough; and a plurality of sidewalls in contact with said bottom surface such that said bottom surface and said plurality of sidewalls define a space, and wherein the introducing step additionally comprises:

flowing said liquid sterilant through said perforations onto said bottom surface to thereby contact with said article; and draining said sterilant through said inlet passages.

24. The method of claim 21, wherein said article has a lumen therein, and wherein the introducing step comprises attaching an adaptor to said lumen and flowing said liquid sterilant through said adaptor and into said lumen.

25. The method of claim 21, wherein said liquid sterilant comprises hydrogen peroxide.

26. The method of claim 21, wherein the sterilizing comprises placing said bottom surface with said article and known volume of sterilant in a diffusion-restricted environment.

27. The method of claim 26, wherein the sterilizing additionally comprises exposing said diffusion-restricted environment to vacuum for a period of time.

28. The method of claim 21, wherein said known quantity of said liquid sterilant vaporizes during the sterilizing.

29. The method of claim 21, wherein the sterilizing occurs within a diffusion restricted environment.

30. The method of claim 29, furthermore comprising the step of restricting diffusion out of said container to create said diffusion restricted environment.

31. The method of claim 21, additionally comprising enclosing said article within a gas permeable material.

32. The method of claim 31, wherein the enclosing step is performed before the vaporizing step.

33. The method of claim 31, wherein the article is enclosed within a gas permeable pouch or container.

34. The method of claim 31, wherein the article and said bottom surface are enclosed within said gas permeable material.

35. The method of claim 31, wherein said gas permeable material comprises CSR-wrap or TYVEK™.

36. The method of claim 21, wherein the vaporizing step comprises heating or reducing pressure.

37. The method of claim 21, additionally comprising exposing the article to plasma after the vaporizing step to enhance efficacy of sterilization or remove residual sterilant.

* * * * *